United States Patent

Parker

[11] 4,017,514
[45] Apr. 12, 1977

[54] HYPOLIPIDEMIC AGENTS

[75] Inventor: Roger Alan Parker, Cincinnati, Ohio

[73] Assignee: Richardson-Merrell Inc., Wilton, Conn.

[22] Filed: June 16, 1975

[21] Appl. No.: 587,044

[52] U.S. Cl. .................. 260/332.2 G; 260/247.1 P; 260/247.2 R; 260/268 H; 260/290 R; 260/293.57; 260/326.82; 260/329 HS; 260/332.3 R; 424/250; 424/263; 424/267; 424/275

[51] Int. Cl.² .................................... C07D 333/24

[58] Field of Search ............ 260/332.2 C, 332.3 R, 260/329 HS, 293.57

[56] References Cited

OTHER PUBLICATIONS

Jakobsen et al. "Chem. Abst." (1964) vol. 60, pp. 6808c–6809b.

Primary Examiner—James O. Thomas, Jr.
Assistant Examiner—A. Siegel
Attorney, Agent, or Firm—L. Ruth Hattan; Eugene O. Retter; George W. Rauchfuss, Jr.

[57] ABSTRACT

Substituted thiophenecarboxylic acids and esters and pharmaceutically acceptable salts thereof of the following general structure are useful as hypolipidemic agents:

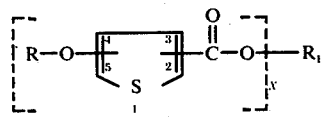

wherein R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl chain of from 1 to 6 carbon atoms, benzyl, phenethyl, pyridyl-methyl, alkane-poly-yl containing from 3 to 6 carbon atoms, 1,2,3,4,5,6-cyclohexanehexayl, and Z; Z is selected from

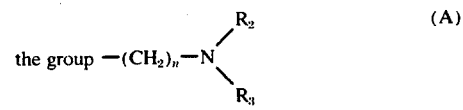

wherein $n$ is the integer 2 or 3; $R_2$ is selected from a straight or branched lower alkyl chain of from 1 to 4 carbon atoms, and alkylcarbonyl wherein the alkyl moiety contains from 1 to 4 carbon atoms and may be straight or branched; $R_3$ is selected from hydrogen and a straight or branched lower alkyl chain of from 1 to 4 carbon atoms with the proviso that when $R_3$ is hydrogen, $R_2$ is alkylcarbonyl; or when $R_2$ is other than alkylcarbonyl, $R_2$ and $R_3$ taken together with the nitrogen atom to which each is attached form a monocyclic heterocyclic group selected from pyrrolidino, piperidino, morpholino, and piperazino; or

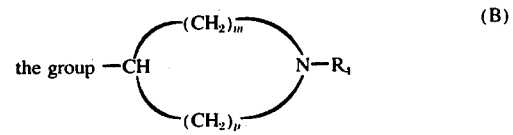

wherein the sum of the integers $m$ and $p$ is equal to from 3 to 5; and $R_4$ is a straight or branched lower alkyl chain of from 1 to 4 carbon atoms; X is an integer of from 1 to 6 with the proviso that when $R_1$ is alkane-poly-yl or 1,2,3,4,5,6-cyclohexanehexayl, X is equal to from 2 to 6, and when $R_1$ is other than alkane-poly-yl or 1,2,3,4,5,6-cyclohexanehexayl, X is equal to 1.

10 Claims, No Drawings

HYPOLIPIDEMIC AGENTS

FIELD OF INVENTION

This invention relates to alkoxy substituted tiophene carboxylic acid and esters and pharmaceutically acceptable salts thereof which are useful as hypolipidemic agents.

SUMMARY OF INVENTION

Compounds of the following general Formula 1 are useful as hypolipidemic agents:

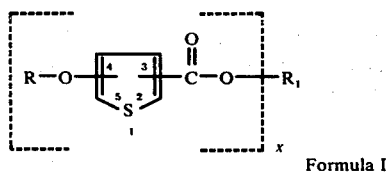

Formula I wherein R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl chain of from 1 to 6 carbon atoms, benzyl, phenethyl, pyridylmethyl, alkane-poly-yl containing from 3 to 6 carbon atoms and from 2 to 6 univalent bonds, 1,2,3,4,5,6- cyclohexanehexayl, and Z; Z is selected from

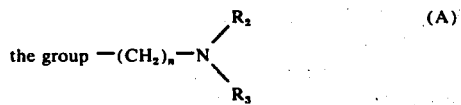

(A)

wherein $n$ is the integer 2 or or 3 $R_2$ is selected from a straight or branched lower alkyl chain of from 1 to 4 carbon atoms and alkylcarbonyl wherein the alkyl moiety contains from 1 to 4 carbon atoms and may be straight or branched; $R_3$ is selected from hydrogen and a straight or branched lower alkyl chain of from 1 to 4 carbon atoms with the proviso that when $R_3$ is hydrogen, $R_2$ is alkyl-carbonyl; or when $R_2$ is other than alkylcarbonyl, $R_2$ and $R_3$ taken together with the nitrogen atom to which each is attached form a monocyclic heterocyclic group selected from pyrrolidino, piperidino, morpholino, and piperazino; or

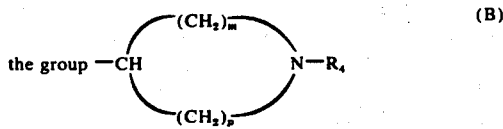

(B)

wherein the sum of the integers as represented by $m$ and $p$ is equal to from 3 to 5, $R_4$ is a straight or branched lower alkyl chain of from 1 to 4 carbon atoms; X is a integer of from 1 to 6 with the proviso that when $R_1$ is alkane-poly-yl or 1,2,3,4,5,6-cyclohexanehexayl, X is equal to from 2 to 6, and when $R_1$ is other than alkane-poly-yl or 1,2,3,4,5,6-cyclohexanehexayl, X is equal to 1.

Pharmaceutically acceptable salts of compounds of general Formula 1 wherein $R_1$ represents hydrogen or a basic group are also included within the scope of this invention.

DETAILED DESCRIPTION OF INVENTION

In the above general Formula 1, the substituent group represented as R—O— may be attached at any of the positions 2-, 3-, 4-, or 5of the thiophene ring, and the acid function may be attached at the 2- or 3-position of the thiophene ring with the proviso that both the R—O— group and the acid function are not attached to the same carbon atom.

As represented herein R may be a straight or branched saturated hydrocarbon chain containing from 10 to 20 carbon atoms in which case the substituent group R—O may be represented as $C_zH_{2z+1}O$ — wherein z is an integer of from 10 to 20, and the hydrocarbon moiety may be straight or branched. The substituent R may also be a straight or branced unsaturated hydrocarbon chain containing from 10 to 20 carbon atoms and from 1 to 4 double bonds and may be represented as $C_zH_{2z-w}O$— wherein z is an integer of from 10 to 20 and w is the integer 1, 3, 5, or 7 as the number of double bonds increases respectively from 1 to 4 in the hydrocarbon chain which may be straight or branched.

Illustrative examples of straight or branched saturated hydrocarbon chains which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl, octadecyl, 3-methyloctadecyl, nonadecyl, and didecyl. Illustrative examples of straight or branched unsaturated hydrocarbon chains containing from 1 to 4 double bonds which R may represent are, for example, 10-undecenyl, 9,12-octadecadienyl, 3,7,11-trimethyl-2,6,10-octatrienyl, 3,7-dimethyl-2,6-octadienyl, 5,9-dimethyl-2,4,8-decatrienyl, 3,7-dimethyloct-6-enyl, 1,2,5,9-tetramethyl-2,4,8-decatrienyl, and 11-didecenyl. Both the cis- and trans- isomers of the unsaturated alkyl groups are included within the scope of this invention.

Illustrative examples of straight or branched lower alkyl chains which $R_1$ may represent as used herein are, for example, methyl, ethyl, n-propyl, isopropyl, n-butyl, tert-butyl, pentyl and hexyl.

Illustrative examples of straight or branched lower alkyl groups which $R_2$, $R_3$ and $R_4$ may represent as used herein are, for example, methyl, ethyl, n-propyl, isopropyl, n-butyl and tert-butyl.

The term alkylcarbonyl which $R_2$ may represent in the compounds described herein is taken to mean a radical having the structure

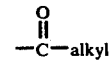

wherein the alkyl moiety contains from 1 to 4 carbon atoms, such as, methyl, thyl, n-butyl, and n-propyl.

The group alkane-poly-yl contains from 3 to 6 carbon atoms and from 2 to 6 univalent bonds. Illustrative examples of alkane-poly-yl groups which $R_1$ may represent in the compounds described herein are, for example, 1,3-propanediyl, 1,2,3-propanetriyl, 1,2-propanediyl, 1,2,3,4,5,6-hexanehexayl, 1,5-pentanediyl, 1,6-hexanediyl.

The term 1,2,3,4,5,6-cyclohexanehexayl is taken to mean a cyclohexane ring with a univalent bond extending from each of the 6 carbon atoms.

Pharmaceutically acceptable salts of the compounds of general Formula 1 wherein $R_1$ represents hydrogen are those formed with any suitable inorganic or organic bases such as those of alkali metals, for example, sodium and potassium; alkaline earth metals, for example, calcium and magnesium, light metals of Group 111 A, for example, aluminum; organic amines such as primary, secondary or tertiary amines, for example, cyclohexylamine, ethylamine and piperidine. The salts can be prepared by conventional means such as by contacting and neutralizing a solution of a compound of Formula 1 having a carboxylic acid group in a polar solvent with the stochiometric quantity of a base, for example, sodium hydroxide.

Pharmaceutically acceptable salts of the compounds of general Formula 1 wherein $R_1$ represents a basic group are those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cynnamic, salicylic and 2-phenoxybenzoic, or sulfonic acids such as, for example, methanesulfonic and 2-hydroxyethane sulfonic acid.

It is apparent from the above general Formula 1 that when $R_1$ is other than alkane-poly-yl or 1,2,3,4,5,6-cyclohexanehexayl, the compounds are alkoxythiophenecarboxylic acid or monoester derivatives are represented by the following general Formula 11, or when $R_1$ is alkane-poly-yl or 1,2,3,4,5,6-cyclohexanehexayl, the compounds are polyester derivatives of alkoxythiophenecarboxylic acid as represented by the following general Formula 111.

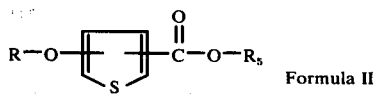

Formula II

In the above general Formula 11, R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; and $R_5$ is selected from hydrogen, a straight or branched lower alkyl chain of from 1 to 6 carbon atoms, such as, methyl, ethyl, propyl, isopropyl, tert-butyl, and pentyl; benzyl; phenethyl; pyridylmethy; and Z; Z is selected from:

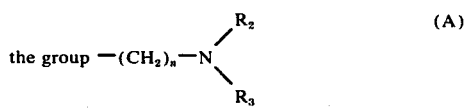

wherein $n$ is an integer of 2 or 3 $R_2$ is selected from a straight or branched lower alkyl chain of from 1 to 4 carbon atoms and alkylcarbonyl wherein the alkyl moiety contains from 1 to 4 carbon atoms; $R_3$ is selected from hydrogen and a straight or branched lower alkyl chain of from 1 to 4 carbon atoms with the proviso that when $R_3$ is hydrogen, $R_2$ is alkylcarbonyl; or when $R_2$ is other than alkylcarbonyl, $R_2$ and $R_3$ together with the nitrogen atom to which each is attached form a monocyclic heterocyclic group selected from pyrrolidino, piperidino, morpholino, and piperazino; or

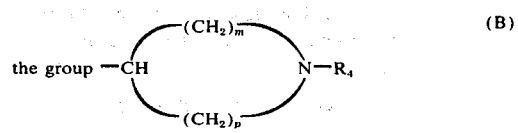

wherein the sum of the integers as represented by $m$ and $p$ is equal to from 3 to 5; and $R_4$ is a straight or branched lower alkyl chain of from 1 to 4 carbon atoms. The pharmaceutically acceptable salts of the compounds of general Formula 11 are within the scope of this invention.

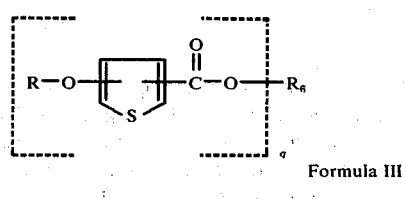

Formula III

In the above Formula 111 R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_6$ is selected from alkane-poly-yl containing from 3 to 6 carbon atoms and from 2 to 6 univalent bonds and 1,2,3,4,5,6-cyclohexanehexayl; and $q$ is an integer of from 2 to 6.

The compounds of general Formulas 11 and 111 represent preferred embodiments of this invention. The compounds of general Formula 11 represent a more preferred embodiment of this invention. Of the compounds of general Formula 11 those wherein $R_5$ is selected from hydrogen, a straight or branched alkyl chain of from 1 to 6 carbon atoms, benzyl and phenethyl are more preferred, of which the benzyl ester is most preferred. Compounds wherein the R—O—group and the acid function are attached at the 5 and 2-positions respectively are preferred.

Illustrative examples of compounds of his invention are, for example, 5-decyloxy-2-thiophenecarboxylic acid, 5-tetradecyl- oxy-2-thiophenecarboxylic acid, 5-(trans-9-octadecenyloxy)-2-thiophenecarboxylic acid, 5-dodecyloxy-2-thiophenecarboxylic acid, 5-tetradecyloxy-2-thiophenecarboxylic acid methyl ester, 5-tetradecyl -oxy-2-thiophenecarboxylic acid ethyl ester, 5-octadecyloxy-2-thiophenecarboxylic acid, 4-dodecyloxy-2-thiophenecarboxylic acid butyl ester, 3-tridecyloxy-2-thiophenecarboxylic acid benzyl ester, 5-hexadecyloxy-2-thiophenecarboxylic acid methyl ester, 2-heptadecyloxy-3-thiophenecarboxylic acid, 4-undecyloxy-3-thiophenecarboxylic acid methyl ester, 5-hexadecyloxy-2-thiophenecarboxylic acid diethylamino ethyl ester, 5-pentadecyloxy-2-thiophenecarboxylic acid 3-pyridylmethyl ester, 5-tetradecyloxy-2-thiophenecarboxylic acid diester with 1,3-propenediol, 5 -hexadecyloxy-2-thiophenecarboxylic acid hexaester with inositol, 4-decyl-2-thiophenecarboxylic acid triester with glycerol, 5-undecyloxy-2thiophenecarboxylic acid ethyl ester, 5-nonadecyloxy-2-thiophenecarboxylic acid phenethyl ester, didecyloxy- 2-thiophenecarboxylic acid propyl ester, 3-didecyloxy 2 thiophenecarboxylic acid 4-pyridylmethyl ester, 4-dodecyloxy- 2 -thiophenecarboxylic acid dipropylamino propyl ester, 5-tetradecyloxy- 2 -thiophenecarboxylic acid piperidinoethyl ester, 4-hexadecyloxy- 2 -thiophenecarboxylic acid morpholinoethyl ester, 5-undecyloxy-3-thiophenecarboxylic acid 4-(N-methyl)-piperidyl ester, 5-tetradecyloxy-2 -thiophenecarboxylic acid 3-pyrolidinyl ester, 5-(10-undecenyloxy)- 2-thiophenecarboxylic acid, 4-(trans-trans- 1,2,5,9-tetramethyl)-2,4,8-decatrienyloxy)-2-thiophenecarboxylic acid ethyl ester, 5-(cis- cis-9,12-octadienyloxy)-3-thiophenecarboxylic acid benzyl ester, 5-(3,7-dimethyloct-6-enyloxy)-2-thiophenecarboxylic acid.

The compounds of this invention are useful as hypolipidemic agents in that they reduce blood lipids, particularly cholesterol and triglycerides without concurrent accumulation of desmosterol. These compounds can be administered to animals, mammals, rats, cats, dogs, pigs, cattle, horses and humans and are useful in the treatment of hyperlipidemic states such as are encountered in patients with cardiovasular diseases that can result in heart failure and stroke. As used herein, the term patient is intended to mean the animal or mammal being treated.

To illustrative the utility of the compounds of this invention young male rats of the Wistar strain initially weighing about 175grams were given free access to a diet which contained 0.15% by weight of test compound, that is, a compound of the general Formulas 1to 111. This diet was prepared by mixing the test compound with commercial Purina Chow. (Trade- mark of Ralston Purina Co., St Louis, Miss. Groups of animals were given these diets for either 4 or 10 days. Control groups of 6 rats each were given Purina Chow to which to test compound had been added. At the end of the treatment period all rats were bled by cardiac puncture, and the plasma was analyzed for cholesterol and triglyceride content. The results are given in the following Table 1.

Table 1

| Test Compound: | 5-(tetradecyloxy)-2-thiophenecarboxylic ylic acid |
| --- | --- |
| Duration of Treatment (Days): | 4 |
| Daily Dose mg/kg (a): | 150 |
| No. Rats: | 6 |
| Plasma Cholesterol % Reduction (b): | 54 |
| Plasma Triglycerides % Reduction (b): | 83 |

(a) Determined by measuring food consumption.
(b) Compared to untreated control rats in the same experiment.

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unite administered can be any lipid lowering effective amount. The quantity of compound administered can vary over a wide range to provide from about 0.5 mg/kg (milligram per kilogram) to about 300 mg/kg of body weight of the patient per day, and preferably from about 10 mg/kg to 30 mg/kg of body weight of the patient per day, to achieve the desired effect. Unit doses can contain from about 50 mg to 1 g of a compound of this invention and may be administered, for example, from 1 to 4 times daily.

The compounds of general Formula 1 wherein $R_1$ is hydrogen are prepared by aromatic nucleophilic substitution [J. March, *Advanced Organic Chemistry: Reactions, Mechanisms, and Structures*, MacGraw-Hill, p. 500 (1968)] as outlined below

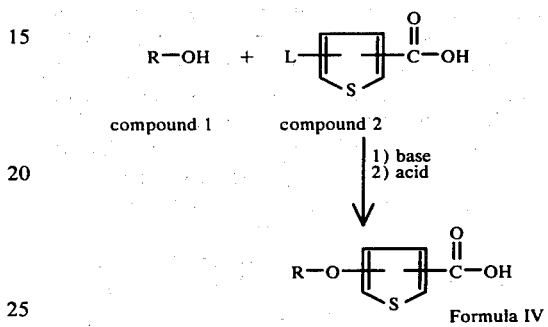

Formula IV

In the above general reaction R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; L represents a leaving group such as nitro, fluoro, chloro, bromo, or iodo, the preferred leaving group being chloro. The substituent group L on compound 2, and R—O— on compounds of Formula IV and the acid function may be attached at the 2-,3-, 4-, or 5-positions of the thiophene ring, with the proviso that both L or R—O— and the acid function are not attached to the same carbon atoms of the thiophene ring.

The above reaction may be carried out with or without a solvent. Suitable solvents for the reaction include benzene, xylene, toluene, chlorinated aromatic hydrocarbons, such as, chlorobenzene, ethers, such as, bis(2-methoxyethyl)ether, 1,2-dimethoxyethane, or anisole, dimethylformamide, dimethylacetamide, 1-methyl-2-pyrrolidone or pyridine. Preferred solvents are xylene and dimethylacetamide. Copper metal or a salt such as cuprous chloride may optionally be added to the reaction. Suitable bases for the reactions include sodium or potassium metal, sodium hydride, potassium amide potassium tert-butylate or other strong bases, such as, potassium carbonate, potassium hydroxide, sodium hydroxide and sodium carbonate. The temperature of the reaction varies from about room temperature, that is, about 25° C to reflux temperature of the solvent, and the reaction time varies from about 1 hour to about 7 days and following completion of the reaction the carboxylate salt derivative is treated with a mineral or organic acid to give compounds of Formula IV.

Alcohols as represented by compound 1 which find use in the above general reaction are commerically available or may be prepared by reduction of the corresponding carboxylic acid or aldehyde. The thiophene carboxylic acid derivatives as represented by compound 2 may be prepared by several methods as described, for example, in the *Chemistry of Heterocyclic*

*Compounds, Thiophene and its Derivatives*, by H. D. Hartough, interscience Publishers, Inc., N. Y., pp. 379–381 (1952).

The compounds of general Formula 1 wherein $R_1$ is hydrogen, and the substituent group R—O— is attached to the 5-position of the thiophene ring and the acid function is attached to the 2-position of the thiophene ring may also be prepared from the corresponding R—O— substituted thiophenecarboxaldehydes by the Cannizzaro reaction as generally described by E. Profft, Monatsber. Deut. Acad. 1, 180–8 (1959) or by oxidation of the of the aldehyde with silver oxide or alkaline permanganate solution as generally described by H. D. Hartough, cited hereinabove, p, 369.

The R—O— substituted thiophene carboxyaldehydes employed in the above described alternate synthesis are obtained by treating an appropriate R—O— substituted thiophene derivative with N-methylformanilide and phosphorous oxychloride followed by water hydrolysis as generally described in Fieser and Fieser Advanced Organic Chemistry, Reinhold Publishing Corporation, New York, p. 821 (1961).

The R—O—substituted thiophene derivatives can be prepared from 3-thiolen-2-one [R. T. Hawkins, J. Heterocyclic Chem. 11, (3), 291–4 (1974)] with a suitable alkyl halide, alkyl mesylate or alkyl tosylate in the presence of a base, for example, sodium hydride, potassium amide, potassium tert-butylate, sodium or potassium metal, potassium carbonate, sodium carbonate, triethylamine or pyridine to yield the 2-alkoxythiophene intermediate. The reaction may be carried out with or without a solvent. Suitable solvents for this reaction include pyridine, benzene, xylene, chlorobenzene, ethers, such as, bis(2-methoxyethyl)ether or anisole, dimethylformamide, dimethylacetamide, and hexamethylphosphoric triamide. The alkyl halide may be for example, alkyl chloride, alkyl bromide, or alkyl iodide. The alkyl moiety in the alkyl halide, the alkyl mesylate, and the alkyl tosylate is a hydrocarbon radical containing from 10 to 20 carbon atoms which may be straight or branched and may be saturated or unsaturated in which case it may contain from 1 to 4 double bonds.

The compounds of general Formula 1 wherein $R_1$ is hydrogen, and the substituent group R—O— is attached to the 5-position of the thiophene ring, and the acid function is attached to the 2-position of the thiophene ring may also be prepared by a Friedel-Crafts acylation of an appropriately R—O— substituted thiophene derivative with acetyl halide, for example, acetyl chloride or acetyl bromide, or acetic anhydride in the presence of an acid catalyst, for example, boron trifluoride-etherate, stannic chloride, zinc chloride, hydriodic acid, or orthophosphoric acid with or without a solvent to give the corresponding 5—R—O—2-acetyl-substituted thiophene derivative. Suitable solvents for this reaction include, for example, methylene chloride, nitromethane and chlorobenzene. Haloform oxidation of the 5—R—O—2-acetyl substituted thiophene derivative with hypohalite solution, for example, lithium hyprochlorite or sodium hyprobromite and aqueous base, for example, sodium hydroxide or potassium hydroxide and subsequent acidification of the reaction mixture with for example, hydrochloric acid will give the 5-alkyloxy-2-thiophene carboxylic acid. The Friedel-Crafts acylation and the haloform oxidation reactions are generally described by H. D. Hartough, cited hereinabove, pages 321 and 364 respectively.

Metalation of the 5—R—O—thiophene derivative with for example, butyllithium, sodium metal, diethyl mercury, ethylmagnesium chloride or sodium amalgam followed by treatment of the reaction mixture with carbon dioxide (that is, dry ice), and subsequent acidification with for example hydrochloric acid, will give the 5-alkyloxy-2-thiophene carboxylic acid. This reaction is generally described by H. D. Hartough, Ibid., at page 365.

Esterification of the thiophene carboxylic acid as represented by the above general Formula IV to give compounds of general Formula 1 wherein $R_1$ is other than hydrogen may be carried out by several methods. For example, compound of Formula IV are converted to the metal salts, for example, sodium or potassium or an amine salt, for example, ammonium salt or triethyl ammonium salt and subsequently reacted with an alkyl halide of the formula halo-$R_1$ or an alkyl sulfate of the formula $R_1SO_4R_1$ or a sulfonate of the formula $R_1O$-$SOR_7$ wherein $R_1$ has the meaning defined in general Formula 1 except that $R_1$ is not hydrogen, and $R_7$ is lower alkyl of from 1 to 4 carbon atoms or substituted aryl, for example, tosyl. Esterification of compounds of general Formula IV may also be carried out by alcoholysis of the substituted thiophenecarboxylic acid chloride, which is formed by reacting the acid with the thionyl chloride, or the substituted thiophenecarboxylic acid imidazolide, which is formed by reacting the acid with N,N'carbonyldiimidazole, with an alcohol of the formula $R_1$—OH wherein $R_1$ has the meaning defined in general Formula 1 except that $R_1$ is not hydrogen. Esterification may also be promoted by the reaction of a substituted thiophenecarboxylic acid compound of general Formula IV with an alcohol of the formula $R_1$—OH wherein $R_1$ has the meaning defined in general Formula 1 except that $R_1$ is not hydrogen and a dehydrating agent, for example, N,N'-dicyclohexylcarbodiimide.

The following specific examples are illustrative of the invention.

EXAMPLE 1

5-(Tetradecyloxy)-2-thiophenecarboxylic acid

A mixture of 21.4 g (0.100 mole) of 1-tetradecanol, 5.9 g (0.146 mole) of sodium hydride (59.5% in oil) and 300 ml of dried xylene is heated to reflux with stirring for 2 hours then allowed to cool after which 7.5 g (0.046 mole ) of 5-chloro-2-thiophenecarboxylic acid is added. The mixture is refluxed for 64 hours after which the mixture is cooled and poured into a water-ice mixture, acidified with acetic acid, and extracted with the addition of ether. The ether is evaporated and aqueous layer extracted 5 times with water: strong ammonia solution (1:1). The combined aqueous extract is acidified with acetic acid. The solid obtained is crystallized twice from hexane to give 5-(tetradecyloxy)-2-thiophene carboxylic acid, M.P. 95°–96° C.

EXAMPLE 2

5-(Hexadecyloxy)-2-thiophenecarboxylic acid

A mixture of 20 g (0.2 mole) of 3-thiolen-2-one [R.T. Hawkins, Journal Heterocyclic Chemistry, 11, (3), 291–4 (1974)], 61.1 g (0.2 mole) of 1-bromohexadecane, and 4.8 g (0.2 mole) of sodium hydride in dry benzene is refluxed with stirring for 24 hours after which the solvent is removed and the product distilled to give 2-hexadecyloxythiophene.

To a cooled mixture of 27 g of N-methylformanilide and 27 g (0.176 mole) of phosphorus oxychloride is added 32.5 g (0.1 mole) of 2-hexadecyloxythiophene. The mixture is warmed to 70° C under vacuum (10 mm Hg). The mixture is allowed to stand at 60°–70° C for 7 hours, the overnight at room temperature after which the mixture is stirred into 100 g of ice. The mixture is extracted into benzene, washed with water, dried over sodium sulfate and distilled in vacuo to give 5-hexadecyloxy-2-thiophenecarboxaldehyde. The carboxaldehyde (7.1 g, 0.02 mole) is stirred vigorously with 4 g of potassium hydroxide in 2.6 ml of water for 24 hours. The mixture is diluted with water and extracted into ether. The aqueous layer is separated and acidified with hydrochloric acid precipitating 5-(hexadecyloxy)-2-thiophenecarboxylic acid.

EXAMPLE 3

5-(Cis-9-octadecenyloxy)-2-thiophenecarboxylic acid

When in Example 1 oleyl alcohol is substituted for 1-tetradecanol, 5-(cis-9-octadecenyloxy)-2-thiophenecarboxylic acid is obtained.

EXAMPLE 4

5-Dodecyloxy-2-thiophenecarboxylic acid

When in Example 2, 1-bromododecane is substituted for 1-bromohexadecane, 5-dodecyloxy-2-thiophenecarboxaldehyde is obtained. The carboxaldehyde (5.9 g, 0.02 mole) is added to brown silver oxide formed from 7.5 g of silver nitrate and 3.5 g of sodium hydroxide in 30 ml of water. The mixture is stirred vigorously overnight at room temperature, and the silver is removed and washed with water. The aqueous solution is acidified with hydrochloric acid to give 5-dodecyloxy-2-thiophenecarboxylic acid.

EXAMPLE 5

5-Tetradecyloxy-2-thiophenecarboxylic acid methyl ester

A mixture of 10.6 g of (0.031 mole) of 5-tetradecyloxy-2-thiophene carboxylic acid, 200 ml of acetone, and 4.3 g (0.031 mole) of potassium carbonate is stirred at room temparature after which 3.9 g (0.031 mole) of dimethyl sulfate is added. The mixture is stirred with heating for about 2½ hours during which time 10 ml of methanol is added. The mixture is then diluted with 100 ml of acetone and filtered. The filtrate is evaporated to dryness to give 5-tetradecyloxy-2-thiophene carboxylic acid methyl ester.

EXAMPLE 6

5-Tetradecyloxy-2-thiophenecarboxylic acid ethyl ester

A mixture of 10.6 g (0.031 mole) of 5-tetradecyloxy-2-thiophene carboxylic acid, 4.3 g (0.034 mole) of potassium carbonate, and dimethylformamide is stirred at room temperature after which 15.6 g (0.10 mole) of ethyl iodide is added. The mixture is heated at 50° C with stirring overnight and poured into water and extracted with the ether. The ether layer is washed with water and salt water and then dried over sodium sulfate, filtered, and the ether is distilled off to give 5-tetradecyloxy-2-thiophenecarboxylic acid ethyl ester.

EXAMPLE 7

5-Octadecyloxy-2-thiophenecarboxylic acid

When in Example 2, 1-bromooctadecane is substituted for 1-bromohexadecane, 2-octadecyloxythiophene is obtained. A mixture of 35.3 g (0.1 mole) of 2-octadecyloxythiophene and 12.3 g (0.12 mole) of acetic anhydride is cooled in an ice bath. While rapidly stirring this mixture, 1.4 g of boron trifluoride etherate is added, and the mixture is heated to 100° C with stirring for 1 hour after which it is cooled to room temperature. Ice water is added, and the mixture is extracted with chloroform. The chloroform solution is evaporated to dryness under reduce pressure to give 2-acetyl-5-octadecyloxythiophene. In 500 ml of 10% aqueous potassium hydroxide 2-acetyl-5-octadecyloxythiophene is combined with 35.0 g (0.6 mole) of lithium hypochlorite. The mixture is stirred vigorously on a steam bath overnight, then allowed to cool to room temperature and extracted with ether. The aqueous extract is acidified with hydrochloric acid to precipitate 5-octadecyloxy-2-thiophenecarboxylic acid.

EXAMPLE 8

5-(3,7,11,15-Tetramethylhexadecyloxy)-2-thiophenecarboxylic acid.

When in Example 2, 1-bromo-3,7,11,15-tetramethyhexadecane is substituted for 1-bromohexadecane, 2-(3,7,11,15-tetramethylhexadecyloxy)thiophene is obtained. A solution of 38.1 g (0.1 mole) of 2-(3,7,11,15-tetramethylhexadecyloxy)-thiophene in 50 ml of anhydrous ether is added over a 4 hour period to 6.0 g of sodium amalgam in 100 ml of anhydrous ether at reflux temperature (36°–39° C) under slight nitrogen pressure. The mixture is refluxed an additional 2 hours, then cooled to room temperature are carbonated by adding freshly crushed dry ice after which 20 ml of ethanol is added dropwise followed by the addition of 50 ml of water. The aqueous solution is separated from the ether layer, filtered and acidified with hydrochloric acid to precipitate 5-(3,7,11,15-tetramethylhexadecyloxy)-2-thiophenecarboxylic acid.

When in Example 1 an alcohol listed below is substituted for 1-tetradecanol, and a thiophenecarboxylic acid listed below is employed, the respective products are obtained.

| Ex. No. | Product | Alcohol | Thiophene carboxylic acid |
|---|---|---|---|
| 9 | 2-didecyloxy-3-thiophenecarboxylic acid | didecanol | 2-bromo-3-thiophenecarboxylic acid |
| 10 | 5-heptadecyloxy-3-thiophenecarboxylic acid | heptadecanol | 5-chloro-3-thiophenecarboxylic acid |
| 11 | 5-decyloxy-2-thiophenecarboxylic acid | decanol | 5-nitro-2-thiophenecarboxylic acid |
| 12 | 4-hexadecyloxy-2-thiophenecarboxylic acid | hexadecanol | 4-fluoro-2-thiophenecarboxylic acid |
| 13 | 5-(10-undecenyloxy-2-thiophenecarboxylic acid | 10-undecen-1-ol | 5-chloro-2-thiophenecarboxylic acid |

-continued

| Ex. No. | Product | Alcohol | Thiophene carboxylic acid |
|---|---|---|---|
| 14 | 5-(trans-3,7-dimethyl-2,6-octadienyloxy)-3-thiophenecarboxylic acid | trans-3,7-dimethyl-2,6-octadien-1-ol | 5-chloro-3-thiophenecarboxylic acid |
| 15 | 5-(cis-cis-9,12-octadecadienyloxy)-2-thiophenecarboxylic acid | cis-cis-9,12-octadecadien-1-ol | 5-chloro-2-thiophenecarboxylic acid |
| 16 | 5-(trans-trans-3,7,11-trimethyl-2,6-10-dodecatrienyloxy)-2-thiophenecarboxylic acid | trans-trans-3,7,-11-trimethyl-2,6-10-dodecatrien-1-ol | 5-chloro-2-thiophenecarboxylic acid |
| 17 | 5-(trans-3,7-dimethyl-2,6-octadienyloxy)-2-thiophenecarboxylic acid | trans-3,7-dimethyl-2,6-octadien-1-ol | 5-chloro-2-thiophenecarboxylic acid |

EXAMPLE 18

5-Tetradecyloxy-2-thiophenecarboxylic acid benzyl ester

When in Example 6, benzyl chloride is substituted for ethyl iodide, 5-tetradecyloxy-2-thiophenecarboxylic acid benzyl is obtained.

EXAMPLE 19

5-Tetradecyloxy-2-thiophenecarboxylic acid phenethyl ester

When in Example 6, β-phenethyl chloride is substituted for ethyl iodide, 5-tetradecyloxy-2-thiophenecarboxylic acid phenethyl ester is obtained.

EXAMPLE 20

5-Tetradecyloxy-2-thiophenecarboxylic acid triester with 1,2,3-propanetriol

A mixture of 3 equivalents of 5-tetradecyloxy-2-thiophene carboxylic acid, 1 equivalent of 1,2,3-propanetriol, and 3 equivalents of N,N'-dicyclohexylcarbodiimide in ether is stirred at room temperature for about 3 days after which the mixture is filtered. The filtrate is washed with water, dried over sodium sulfate, filtered and evaporated to dryness to give 5-tetradecyloxy-2-thiophenecarboxylic acid triester with 1,2,3-propanetriol.

EXAMPLE 21

5-Dodecyloxy-2-thiophenecarboxylic acid hexaester with inositol

When in Example 20, 6 equivalents of 5-dodecyloxy-2-thiophenecarboxylic acid is substituted for 5-tetradecyloxy-2-thiophenecarboxylic acid, 1 equivalent of inositol is substituted for 1,2,3-propanetriol, and 6 equivalents of N,N'-dicyclohexylcarbodiimide is used, 5-dodecyloxy-2-thiophenecarboxylic acid hexaester with inositol is obtained.

EXAMPLE 22

5-Tetradecyloxy-2-thiophenecarboxylic acid sodium salt

To 20.4 g (0.06 mole) of 5-tetradecyloxy-2-thiophenecarboxylic acid in 500 ml of methanol is added 5.4 g (0.10 mole) of sodium methoxide. The mixture is refluxed, and the methanol is distilled off being replaced by water. The aqueous solution is cooled, the precipitate collected, and dried to give 5-tetradecyloxy-2-thiophenecarboxylic acid sodium salt.

EXAMPLE 23

An illustrative composition for tablets is as follows:

| | | Per Tablet |
|---|---|---|
| (a) | 5-(tetradecyloxy)-2-thiophenecarboxylic acid | 100.0 mg |
| (b) | wheat starch | 15.0 mg |
| (c) | lactose | 33.5 mg |
| (d) | magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 24

An illustrative composition for a parenteral injection is the following wherein the quantities are on a weight to volume basis.

| | | Amount |
|---|---|---|
| (a) | 5-(tetradecyloxy)-2-thiophenecarboxylic acid sodium salt | 100.0 g |
| (b) | sodium chloride | q.s. |
| (c) | water for injection to make | 20 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

EXAMPLE 25

An illustrative composition for hard gelatin capsules is as follows:

| | | Amount |
|---|---|---|
| (a) | 5-(tetradecyloxy)-2-thiophenecarboxylic acid | 200.0 mg |
| (b) | talc | 35.0 mg |

The composition is prepared by passing the dry powders of (a) and (b) through a fine mesh screen and mixing them well. The powder is then filled into No. O hard gelatin capsules at a net fill of 235 mg per capsule.

EXAMPLE 26

An illustrative composition for pills is the following:

|   |   | Per Pill |
|---|---|---|
| (a) | 5-(tetradecyloxy)-2-thiophenecarboxylic acid | 200 mg |
| (b) | corn starch | 130 mg |
| (c) | liquid glucose | 20 ml |

The pills are prepared by blending the active ingredient (a) and the corn starch then adding the liquid glucose with thorough kneading to form a plastic mass from which the pills are cut and formed.

I claim:

1. A compound selected from the formula:

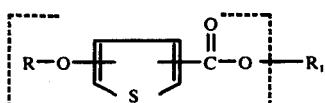

wherein R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl chain of from 1 to 6 carbon atoms, benzyl, phenethyl, alkane-poly-yl containing from 3 to 6 carbon atoms and from 2 to 6 univalent bonds, 1,2,3,4,5,6-cyclohexanehexayl, and Z; Z is the group

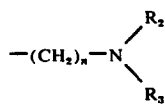

wherein $n$ is the integer 2 or 3; $R_2$ is selected from a straight or branched lower alkyl chain of from 1 to 4 carbon atoms and alkylcarbonyl wherein the alkyl moiety contains from 1 to 4 carbon atoms and may be straight or branched; $R_3$ is selected from hydrogen and a straight or branched lower alkyl chain of from 1 to 4 carbon atoms with the proviso that when $R_3$ is hydrogen, $R_2$ is alkylcarbonyl; X is an integer of from 1 to 6 with the proviso that when $R_1$ is alkane-poly-yl or 1,2,3,4,5,6-cyclohexanehexayl, X is equal to from 2 to 6, and when $R_1$ is other than alkane-poly-yl or 1,2,3,4,5,6-cyclohexanehexayl, X is equal to 1; and pharmaceutically acceptable salts thereof.

2. A compound of claim 1 selected from the formula:

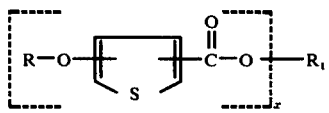

wherein R is selected from a straight or branched saturated hydrocarbon chain containing from 10 to 20 carbon atoms and a straight or branched unsaturated hydrocarbon chain containing from 10 to 20 carbon atoms and from 1 to 4 double bonds; $R_1$ is selected from hydrogen, a straight or branched lower alkyl chain of from 1 to 6 carbon atoms, benzyl, phenethyl, alkane-poly-yl containing from 3 to 6 carbon atoms and from 2 to 6 univalent bonds and 1,2,3,4,5,6-cyclohexanehexayl; and pharmaceutically acceptable salts thereof.

3. A compound of claim 1 wherein $R_1$ is the group

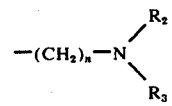

wherein $n$ is the integer 2 or 3, and each of $R_2$ and $R_3$ is a straight or branched lower alkyl chain of from 1 to 4 carbon atoms.

4. A compound of claim 2 wherein X is equal to 1.

5. A compound of claim 4 wherein $R_1$ is benzyl.

6. A compound of claim 2 wherein X is equal to from 2 to 6.

7. A compound of claim 1 selected from the formula:

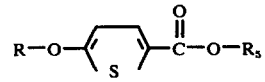

wherein R is selected from a straight or branched saturated hydrocarbon chain containing from 10 to 20 carbon atoms and a straight or branched unsaturated hydrocarbon chain containing from 10 to 20 carbon atoms and from 1 to 4 double bonds, and $R_5$ is selected from hydrogen, a straight or branched lower alkyl chain of from 1 to 6 carbon atoms, benzyl, phenethyl, and Z; Z is the group 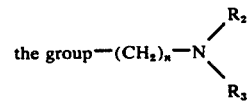

wherein $n$ is an integer of 2 or 3; $R_2$ is selected from a straight or branched lower alkyl chain of from 1 to 4 carbon atoms and alkylcarbonyl wherein the alkyl moiety contains from 1 to 4 carbon atoms; $R_3$ is selected from hydrogen and a straight or branched lower alkyl chain of from 1 to 4 carbon atoms with the proviso that when $R_3$ is hydrogen, $R_2$ is alkylcarbonyl; and pharmaceutically acceptable salts thereof.

8. A compound of claim 7 selected from the formula:

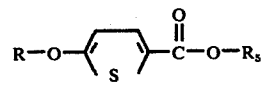

wherein R is selected from a straight or branched saturated hydrocarbon chain containing from 10 to 20 carbon atoms and a straight or branched unsaturated hydrocarbon chain containing from 10 to 20 carbon atoms and from 1 to 4 double bonds, and $R_5$ is selected from hydrogen, a straight or branched lower alkyl chain of from 1 to 6 carbon atoms, benzyl and phenethyl; and pharmaceutically acceptable salts thereof.

9. A compound of claim 8 wherein $R_5$ is benzyl.

10. A compound of claim 8 which is 5-(tetracecyloxy)-2-thiophenecarboxylic acid.

* * * * *

UNITED STATES PATENT AND TRADEMARK OFFICE
CERTIFICATE OF CORRECTION

PATENT NO. : 4,017,514
DATED : April 12, 1977
INVENTOR(S) : Roger Alan Parker

It is certified that error appears in the above-identified patent and that said Letters Patent are hereby corrected as shown below:

Column 1, line 5 "tiophene" should read "thiophene". Column 2, line 16 "R-0" should read "R-O-"; line 18 "branced" should read "branched"; line 61 "thyl" should read "ethyl". Column 4, line 48 "of his" should read "of this". Column 5, line 23 "cardiovasular" should read "cardiovascular"; line 27 "To illustrative" should read "To illustrate; line 34" St. Louis, Miss." should read "St. Louis, Missouri"; line 37 "to test" should read "no test"; line 65 "unite" should read "unit". Column 9, line 6 "the overnight" should read "then overnight". Column 10, line 36, 37 "tetramethyhexadecane" should read "tetramethylhexadecane"; line 45 "are carbonated" should read "and carbonated".

Signed and Sealed this

Fourteenth Day of February 1978

[SEAL]

Attest:

RUTH C. MASON
Attesting Officer

LUTRELLE F. PARKER
Acting Commissioner of Patents and Trademarks